US008649840B2

(12) United States Patent
Sheppard, Jr. et al.

(10) Patent No.: US 8,649,840 B2
(45) Date of Patent: Feb. 11, 2014

(54) ELECTROCHEMICAL BIOSENSORS AND ARRAYS

(75) Inventors: Norman F. Sheppard, Jr., New Ipswich, NH (US); John T. Santini, Jr., North Chelmsford, MA (US)

(73) Assignee: Microchips, Inc., Lexington, MA (US)

( * ) Notice: Subject to any disclaimer, the term of this patent is extended or adjusted under 35 U.S.C. 154(b) by 1564 days.

(21) Appl. No.: 12/134,966

(22) Filed: Jun. 6, 2008

(65) Prior Publication Data

US 2008/0302659 A1 Dec. 11, 2008

Related U.S. Application Data

(60) Provisional application No. 60/942,594, filed on Jun. 7, 2007.

(51) Int. Cl.
*A61B 5/05* (2006.01)
(52) U.S. Cl.
USPC .......................................................... 600/345
(58) Field of Classification Search
None
See application file for complete search history.

(56) References Cited

U.S. PATENT DOCUMENTS

| | | | |
|---|---|---|---|
| 4,703,756 A * | 11/1987 | Gough et al. ................. | 600/347 |
| 4,874,500 A | 10/1989 | Madou et al. | |
| 5,165,407 A | 11/1992 | Wilson et al. | |
| 5,200,051 A | 4/1993 | Cozzette et al. | |
| 5,252,294 A | 10/1993 | Kroy et al. | |
| 5,254,081 A | 10/1993 | Maurer et al. | |
| 5,262,127 A | 11/1993 | Wise et al. | |
| 5,304,293 A | 4/1994 | Tierney et al. | |
| 5,366,454 A | 11/1994 | Currie et al. | |
| 5,493,177 A | 2/1996 | Muller et al. | |
| 5,504,026 A | 4/1996 | Kung | |
| 5,585,069 A | 12/1996 | Zanzucchi et al. | |
| 5,605,662 A | 2/1997 | Heller et al. | |
| 5,782,799 A | 7/1998 | Jacobsen et al. | |
| 5,798,042 A | 8/1998 | Chu et al. | |
| 5,807,375 A * | 9/1998 | Gross et al. ................. | 604/890.1 |
| 5,824,204 A | 10/1998 | Jerman | |
| 5,843,767 A | 12/1998 | Beattie | |
| 5,989,445 A | 11/1999 | Wise et al. | |
| 6,081,736 A * | 6/2000 | Colvin et al. ................. | 600/377 |
| 6,083,763 A | 7/2000 | Balch | |
| 6,140,740 A | 10/2000 | Porat et al. | |
| 6,251,688 B1 | 6/2001 | Erb et al. | |
| 6,256,522 B1 | 7/2001 | Schultz | |
| 6,284,125 B1 * | 9/2001 | Hodges et al. ................. | 205/775 |
| 6,328,699 B1 | 12/2001 | Eigler et al. | |
| 6,366,794 B1 | 4/2002 | Moussy et al. | |
| 6,384,353 B1 | 5/2002 | Huang et al. | |
| 6,461,331 B1 | 10/2002 | Van Antwerp | |
| 6,480,730 B2 | 11/2002 | Darrow et al. | |
| 6,491,666 B1 | 12/2002 | Santini, Jr. et al. | |
| 6,512,939 B1 * | 1/2003 | Colvin et al. ................. | 600/347 |
| 6,527,762 B1 | 3/2003 | Santini, Jr. et al. | |
| 6,551,838 B2 | 4/2003 | Santini, Jr. et al. | |
| 6,571,125 B2 | 5/2003 | Thompson | |
| 6,666,821 B2 | 12/2003 | Keimel | |
| 6,669,683 B2 | 12/2003 | Santini, Jr. et al. | |
| 6,673,596 B1 | 1/2004 | Sayler | |
| 6,702,857 B2 | 3/2004 | Brauker et al. | |
| 6,741,877 B1 | 5/2004 | Shults et al. | |
| 6,773,429 B2 * | 8/2004 | Sheppard et al. ........... | 604/891.1 |
| 6,808,522 B2 | 10/2004 | Richards et al. | |
| 6,827,250 B2 | 12/2004 | Uhland et al. | |
| 6,903,433 B1 | 6/2005 | McFarland et al. | |
| 6,908,770 B1 | 6/2005 | McDevitt et al. | |
| 6,968,743 B2 | 11/2005 | Rich et al. | |
| 6,973,718 B2 | 12/2005 | Sheppard, Jr. et al. | |
| 7,004,928 B2 | 2/2006 | Aceti et al. | |
| 7,025,760 B2 | 4/2006 | Miller et al. | |
| 7,063,782 B2 * | 6/2006 | Wayment et al. .............. | 205/792 |
| 7,070,592 B2 | 7/2006 | Santini, Jr. et al. | |
| 7,125,382 B2 | 10/2006 | Zhou et al. | |
| 7,226,442 B2 | 6/2007 | Sheppard, Jr. et al. | |
| 7,410,616 B2 | 8/2008 | Santini, Jr. et al. | |
| 7,413,846 B2 | 8/2008 | Maloney et al. | |
| 7,455,667 B2 | 11/2008 | Uhland et al. | |

(Continued)

FOREIGN PATENT DOCUMENTS

WO 99/03684 A1 1/1999

OTHER PUBLICATIONS

Plamen Atanasov, Ebtisam Wilkins. In vivo rechargeable glucose biosensors. Sensors and Actuators B: Chemical vol. 36, Issues 1-3, Oct. 1996, pp. 435-447. Proceedings of the Sixth International Meeting on Chemical Sensors.*
Bioelectrochemistry M. Pescheck, J. Schrader, D. Sell. Novel electrochemical sensor system for monitoring metabolic activity during the growth and cultivation of prokaryotic and eukaryotic cells. Bioelectrochemistry vol. 67, Issue 1, Sep. 2005, pp. 47-55.*
Garg, "Improved Glucose Excursions Using an Implantable Real-Time Continuous Glucose Sensor in Adults With Type 1 Diabetes," Diabetes Care, vol. 27, No. 3 (Mar. 2004).

(Continued)

*Primary Examiner* — Robert A Wax
*Assistant Examiner* — Olga V Tcherkasskaya
(74) *Attorney, Agent, or Firm* — Sutherland Asbill & Brennan LLP

(57) ABSTRACT

Electrochemical sensor devices are provided, in various amperometric, potentiometric, and conductometric sensor device configurations. An amperometric sensor device may include a structural body which has at least one reservoir that has at least one opening; a working electrode located within the reservoir; analyte sensor chemistry located within the reservoir and deposited on at least the working electrode; an auxiliary electrode located outside of the reservoir; a reference electrode; at least one reservoir cap closing the opening to isolate the working electrode and analyte sensor chemistry within the reservoir and to prevent an analyte outside of the reservoir from contacting the analyte sensor chemistry; and means for rupturing or displacing the reservoir cap to permit the analyte from outside of the reservoir to contact the analyte sensor chemistry.

25 Claims, 8 Drawing Sheets

(56) References Cited

U.S. PATENT DOCUMENTS

| | | |
|---|---|---|
| 2002/0072734 A1 | 6/2002 | Liedtke |
| 2004/0182722 A1* | 9/2004 | Blomberg et al. ............ 205/775 |
| 2005/0049472 A1 | 3/2005 | Manda et al. |
| 2005/0096587 A1* | 5/2005 | Santini et al. .................. 604/66 |
| 2005/0100937 A1 | 5/2005 | Holmes |
| 2005/0245795 A1* | 11/2005 | Goode et al. .................. 600/302 |
| 2005/0267440 A1 | 12/2005 | Herman et al. |
| 2006/0004272 A1 | 1/2006 | Shah et al. |
| 2006/0025748 A1 | 2/2006 | Ye |
| 2006/0036143 A1* | 2/2006 | Brister et al. ................. 600/345 |
| 2006/0057737 A1 | 3/2006 | Santini, Jr. et al. |
| 2006/0076236 A1* | 4/2006 | Shah et al. ............... 204/403.01 |
| 2006/0171989 A1 | 8/2006 | Prescott et al. |
| 2008/0015494 A1 | 1/2008 | Santini, Jr. et al. |
| 2008/0033260 A1 | 2/2008 | Sheppard, Jr. et al. |
| 2008/0156661 A1 | 7/2008 | Cooper et al. |

OTHER PUBLICATIONS

Grayson, et al. "A BioMEMS Review: MEMS Technology for Physiologically Integrated Devices," Proceedings of the IEEE, vol. 92, No. 1 (Jan. 2004).

Maloney, et al., "Electrothermally activated microchips for implantable drug delivery and biosensing," Journal of Controlled Release 109:244-255 (2005).

* cited by examiner

ELECTROCHEMICAL BIOSENSORS AND ARRAYS

CROSS-REFERENCE TO RELATED APPLICATION

This application claims the benefit of U.S. Provisional Application Ser. No. 60/942,594 entitled "Electrochemical Biosensors and Arrays," filed Jun. 7, 2007, which is incorporated herein by reference.

BACKGROUND OF THE INVENTION

This invention relates generally to sensor devices, and more particularly to electrochemical sensors and sensor arrays. These sensors and sensor arrays may be packaged for medical implant applications.

U.S. Pat. No. 6,551,838 and U.S. Patent Application Publication No. 2005/0096587 to Santini, et al., which are incorporated herein by reference, describe sensors and sensor components stored in one or an array of discrete, protective reservoirs, which can be selectively and actively opened to expose the sensor or component to a fluid environment outside of the reservoir. In one example, the sensor is a chemical sensor and part of an implantable medical device for detecting glucose or other analytes in vivo. In one case, these reservoirs may be closed off by a reservoir cap, or lid, that can be disintegrated by selective application of an electric current.

U.S. Patent Application Publication No. 2006/0076236 to Shah et al., which is incorporated herein by reference, also discloses fabrication of multi-sensor arrays. The long-term analyte sensors include a plurality of analyte contacting sensor elements and a protection membrane that is controllable.

It would be desirable to provide improved sensor devices. For example, it would be advantageous to improve sensing accuracies, increase production and operation efficiencies, and extend the useful life of the sensor(s), while minimizing medical implant device size for ease of implantation in a patient. In particular, it would be desirable to package sensors in ways that improve sensing accuracies, increase production and operation efficiencies, extend the useful life of the sensor(s), and/or reduce medical implant device size for ease of implantation in a patient.

SUMMARY OF THE INVENTION

Improved electrochemical sensor devices are provided. The sensor devices may be useful, for example, in medical applications, such as implantable medical devices, or in non-medical applications.

In one aspect, an amperometric sensor device is provided. In one embodiment, the amperometric sensor device includes a structural body which comprises at least one reservoir that has at least one opening in the structural body; a working electrode located within the reservoir; analyte sensor chemistry located within the reservoir and deposited on at least the working electrode; an auxiliary electrode located outside of the reservoir; a reference electrode; at least one reservoir cap closing the at least one opening to isolate the working electrode and analyte sensor chemistry within the reservoir and to prevent an analyte outside of the reservoir from contacting the analyte sensor chemistry; and means for rupturing or displacing the reservoir cap to permit the analyte from outside of the reservoir to contact the analyte sensor chemistry.

In another aspect, potentiometric sensor devices are provided. In one embodiment, the potentiometric sensor device includes a structural body which comprises a plurality of reservoirs that each have at least one opening in the structural body; at least one indicator electrode located within the plurality of reservoirs; at least one reference electrode located within the plurality of reservoirs; at least one reservoir cap closing the at least one opening of each of the plurality of reservoirs, to isolate the at least one indicator electrode and the at least one reference electrode within the plurality of reservoirs and to prevent an analyte, such as an ion of interest, outside of the reservoirs from contacting the at least one indicator electrode and the at least one reference electrode; and means for rupturing or displacing the reservoir caps to permit the analyte from outside of the reservoir to contact the at least one indicator electrode and the at least one reference electrode, wherein an electrical potential which can be developed between the at least one indicator electrode and the at least one reference electrode provides a sensor signal indicative of a concentration of the analyte. In another embodiment, the at least one reference electrode is located outside of the plurality of reservoirs.

In still another aspect, a conductometric sensor device is provided. In one embodiment, the conductometric sensor device includes a structural body which comprises at least one reservoir that has at least one opening in the structural body; an electrode pair located within the reservoir; a biological recognition element or other selectively sensitive material located within the reservoir and deposited on the electrode pair; at least one reservoir cap closing the at least one opening to isolate the electrode pair and the biological recognition element within the reservoir and to prevent an analyte outside of the reservoir from contacting the biological recognition element; and means for rupturing or displacing the at least one reservoir cap to permit the analyte from outside of the reservoir to contact the biological recognition element.

A device may include arrays of two or more individual sensors, of the same or mixed types.

DETAILED DESCRIPTION OF THE INVENTION

Figure 1:
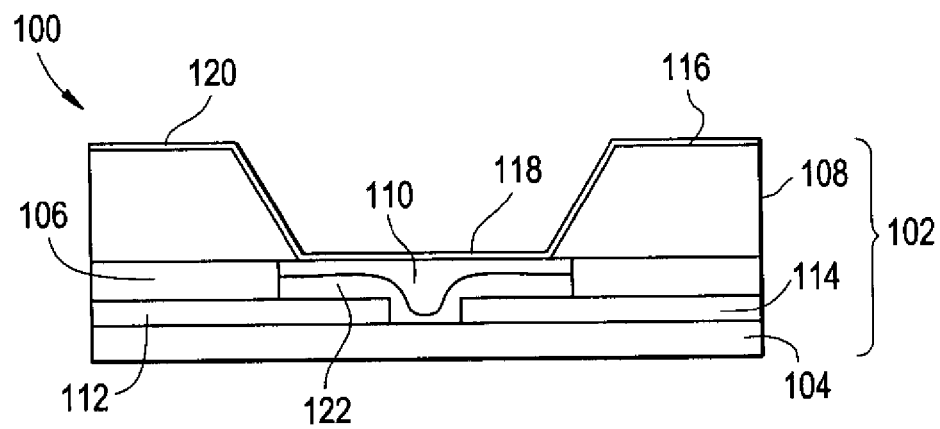
FIG. 1 is a side cross-sectional view of an embodiment of an amperometric sensor device.

Electrochemical sensor devices are provided in packaging/configurations to address one or more of the needs described above. For example, sensor electrodes have been designed and arranged to improve sensor output, enhance sensor useful life, and permit reduced implant device dimensions.

In one aspect, the present device, which may be a microchip package, is used to protect biosensors from exposure to adverse environments by encapsulating them within a reservoir or reservoirs until needed. In this way a continuous monitor can be constructed by utilizing the protected sensors in succession as their operational lifetimes are reached. The most straightforward approach to construction of the monitor is to contain each individual sensor within one reservoir. However, there may be reasons to consider different configurations where (i) the individual electrodes making up a sensor are not contained within the same reservoir, or (ii) a subset of the electrodes making up a sensor are not contained in a reservoir at all. These may be important for example when trying to reduce the size of an implanted sensing device.

In certain embodiments, the electrochemical sensor devices include a structural body which comprises at least one reservoir, or more typically an array of two or more discrete reservoirs, each reservoir having at least one opening in the structural body; one or more of the electrodes of one or more chemical sensors located within the reservoir; at least one discrete reservoir cap closing the at least one opening of each reservoir to isolate the electrode(s) (and associated sensor chemistry, if present) that are located within the reservoir and to prevent external environmental components (e.g., an analyte) outside of the reservoir from contacting the electrode therein; and activation means for rupturing or displacing the reservoir cap to permit the external environmental components (e.g., an analyte) to contact the electrode. In exemplary embodiments, the discrete reservoir caps are in register with predefined openings in the structural body.

In certain embodiments, the structural body (which sometimes may be referred to as the "substrate"), the reservoirs, the reservoir caps, and the activation means for rupturing or displacing the reservoir cap, and how these various components may be packaged together to form hermetically sealed reservoir devices, are described, for example, in U.S. Pat. No. 6,527,762 (which describes thermal means for reservoir cap rupture); U.S. Pat. No. 6,551,838; U.S. Pat. No. 6,976,982 (which describes flexible substrate/body structures); U.S. Pat. No. 6,827,250 (which describes hermetic sealed reservoir structures and sealing methods); U.S. Patent Application Publication No. 2004/0121486 (which describes electrothermal ablation means for reservoir cap disintegration); U.S. Patent Application Publication No. 2006/0057737 (which describes reservoir/structural body designs with multiple discrete reservoir caps closing off a single reservoir opening); U.S. Patent Application Publication No. 2006/0115323 (which describes hermetic sealed reservoir structures and compression cold weld sealing methods); and U.S. Patent Application Publication No. 2005/0096587. These patents and patent applications are incorporated herein by reference.

In a certain embodiment, the reservoir cap is formed of a conductive material, such as a metal film, through which an electrical current can be passed to electrothermally ablate it, as described in U.S. Patent Application Publication No. 2004/0121486 to Uhland, et al. In this embodiment, the reservoir cap itself serves both as a structural barrier for isolating the contents of the reservoir from substances outside of the reservoir and as the heating element. Representative examples of suitable reservoir cap materials include gold, copper, aluminum, silver, platinum, titanium, palladium, various alloys (e.g., Au/Si, Au/Ge, Pt—Ir, Ni—Ti, Pt—Si, SS 304, SS 316), and silicon doped with an impurity to increase electrical conductivity, as known in the art. The reservoir cap may be in the form of a multi-layer structure, such as a multi-layer/laminate structure of platinum/titanium/platinum. The reservoir cap is operably (i.e., electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated (ruptured or disintegrated). The heating may be rapid and substantially instantaneous upon application of an electric current through the reservoir cap, such that no substantial heating of substances (e.g., sensor chemistry, patient tissues) adjacent to the reservoir cap occurs. In one embodiment, the reservoir cap and the conductive leads are formed of the same material, and the temperature of the reservoir cap increases locally under applied current because the reservoir cap is suspended in a medium that is less thermally conductive than the substrate. Alternatively, the reservoir cap and conductive leads are formed of the same material, and the reservoir cap has a smaller cross-sectional area in the direction of electric current flow, where the increase in current density through the reservoir cap causes an increase in localized heating. The reservoir cap alternatively can be formed of a material that is different from the material forming the leads, wherein the material forming the reservoir cap has a different electrical resistivity, thermal diffusivity, thermal conductivity, and/or a lower melting temperature than the material forming the leads. Various combinations of these embodiments can be employed. For example, the reservoir cap and the input and output leads may be designed to provide (i) an increase in electrical current density in the reservoir cap relative to the current density in the input and output leads, upon the application of electrical current, (ii) that the material forming the reservoir cap has a different electrical resistivity, thermal diffusivity, thermal conductivity, and/or a lower melting temperature than the material forming the input and output leads, or (iii) both (i) and (ii).

In another embodiment, the reservoir cap is configured as an anode and the device further includes a cathode, along with electrical circuitry, a power source, and controls for applying an electric potential between the cathode and anode in an electrically conductive fluid environment (e.g., in vivo) to cause the reservoir cap to disintegrate as described in U.S. Pat. No. 5,797,898 to Santini Jr. et al.

In still another embodiment, the reservoir cap is configured to rupture by heating using a separate resistive heating element, which may be located either inside the reservoir or outside the reservoir, generally adjacent to the reservoir cap, as described for example in U.S. Pat. No. 6,527,762 to Santini Jr. et al.

The International Union of Pure and Applied Chemistry defines an electrochemical biosensor as "a self-contained integrated device, which is capable of providing specific quantitative or semi-quantitative analytical information using a biological recognition element (biochemical receptor) which is retained in direct spatial contact with an electrochemical transduction element." See Thevenot, et al., "Electrochemical Biosensors: Recommended Definitions And Classification", *Pure Appl. Chem.*, Vol. 71, No. 12, pp. 2333±2348, 1999. The present electrochemical biosensor devices can be classified as four types: amperometric, potentiometric, surface charge using field-effect transistors, and conductometric.

The term "biosensor" as used herein is not to be construed as being limited to sensors for medical applications. The sensors device structures described herein may be useful in non-medical applications.

Amperometric Sensor Device

Amperometric biosensors directly measure current produced by the oxidation or reduction of an electroactive species at a suitably polarized electrode. An amperometric biosensor can include three electrodes: a working electrode, a reference electrode, and an auxiliary electrode (sometimes referred to as a counter electrode). Suitable instrumentation is used to maintain the working electrode at a controlled potential relative to the reference electrode. In some cases, the amperometric biosensor is constructed with two electrodes where the functions of the reference electrode and the auxiliary electrode are combined. The biosensors' biological recognition element is often—though not in all embodiments—an enzyme for which the analyte of interest is a biochemical substrate. Amperometric sensors exploit the fact that many co-substrates or products of the reaction catalyzed by the enzyme are electroactive. These sensors serve to measure the concentration of a co-substrate or product in the enzyme layer. In the presence of the analyte, the concentration of the co-substrate will decrease and that of the product will increase. The resulting change in sensor current can be related to the analyte concentration through a suitable calibration. Representative examples of suitable enzymes may include glucose oxidase, glucose dehydrogenase, NADH oxidase, uricase, urease, creatininase, sarcosine oxidase, creatinase, creatine kinase, creatine amidohydrolase, cholesterol esterase, cholesterol oxidase, glycerol kinase, hexokinase, glycerol-3-phosphate oxidase, lactate oxidase, lactate dehydrogenase, alkaline phosphatase, alanine transaminase, aspartate transaminase, amylase, lipase, esterase, gamma-glutamyl transpeptidase, L-glutamate oxidase, pyruvate oxidase, diaphorase, bilirubin oxidase, and mixtures thereof. An amperometric biosensor could be constructed without an enzyme layer, for example if the biosensor is configured to measure oxygen.

It is believed that if certain embodiments of reservoir-device protected amperometric sensors were constructed in which the working and auxiliary electrodes are located inside the reservoir and the reference electrode is located outside of the reservoir, such a sensor may have operational difficulties. For example, there may be relatively high electrical impedance between the reference and working electrodes before the reservoir is opened due to a lack of fluid communication between the inside of an unopened reservoir and the surrounding environment, the distance from the reference electrode to the working electrode being considerably greater than from the auxiliary to working electrode, and the auxiliary and working electrodes both being located under the sensor chemistry. Accordingly, improved configurations are now provided as described herein.

In these proposed new configurations, the amperometric sensor's working electrode is contained within a reservoir in order to protect the biological recognition element and other parts of the sensor chemistry from the in vivo environment, while the other electrodes, such as the reference and auxiliary electrodes, making up the sensor's electrochemical cell are variously located inside or outside of the same or different reservoirs as the working electrode, as described herein. In addition to an enzyme (or other biological recognition element) layer, the sensor chemistry typically includes one, two, three, or more polymer layers deposited over the working electrode effective to block interfering substances, to improve the linearity, range and specificity of the sensor, and in some cases, to modulate the properties (e.g., vascularity) of the sensor interface with surrounding tissue. Each layer may provide one or more of these functionalities.

It is advantageous to contain the working electrode in a sealed reservoir for selective exposure (such as at the precise time the electrode is needed for a particular sensor to function) in order to protect the working electrode against (i) fouling of the outer layer of the sensor by proteins and cells which influence transport of analyte to the enzyme layer, (ii) degradation of the enzyme by the hydrogen peroxide produced by oxidase enzymes, (iii) degradation of polymer layers, for example, the hydrolysis of ester linkages of polyurethane membranes, and (iv) degradation processes mediated by cells of the immune system (e.g., macrophages, foreign body giant cells). In addition, hermetically sealed reservoirs enable the environment (e.g., inert gas atmosphere, humidity) inside the sealed reservoir to be controlled, which may lead to a longer lifetime of the sensor.

In one embodiment, the amperometric sensor is a glucose biosensor based on the enzyme glucose oxidase. The enzyme-catalyzed conversion of analyte (e.g., glucose) yields a reaction product (e.g., hydrogen peroxide) that is redox active. (Alternatively, the catalytic activity of the enzyme may result in the consumption of a redox-active co-substrate, such as oxygen in the glucose sensor.) The oxidation or reduction of the redox active compound at a suitably polarized electrode produces a current that can be related back to the analyte concentration.

In one embodiment, an amperometric sensor may be constructed with two electrodes. The same considerations apply as to placement of the working electrode and combined reference/auxiliary in the same or different reservoirs. In an embodiment, the electrodes may include elongated configurations, e.g., a "wire sensor", as described in U.S. Pat. No. 5,165,407 to Wilson et al.

The particular sensors packaged as described herein may take a variety of different forms. In some embodiments, the sensors are tailored for glucose sensing. In a certain embodiment, the present packaged sensor device may include electrodes and glucose sensor chemistries as described in U.S. Pat. No. 6,881,551 to Heller et al. or as described in U.S. Pat. No. 4,890,620 to Gough et al. In other embodiments, the packaged sensor device may include a differential oxygen sensor, as described for example in U.S. Pat. No. 4,781,798.

In a preferred embodiment, the amperometric sensor utilizes three electrodes. The three electrode electrochemical "cell" has working, auxiliary and reference electrodes. The working electrode is where the desired analyte is oxidized or reduced, yielding the sensor current. The reference electrode is used to sense the potential in the solution; the external circuitry (potentiostat) establishes a fixed potential between the reference electrode and the working electrode. The reference electrode desirably is in close proximity to the working electrode to reduce any resistive (IR) potential drops, which may change the working electrode potential. The auxiliary electrode sinks or sources the working electrode current. The auxiliary electrode typically is equal in area to or larger in area than the working electrode in order to reduce the current density and overpotential at the auxiliary electrode.

In certain embodiments of the present devices and methods, the working electrode is located within a reservoir that is sealed and can be selectively unsealed or opened. In a preferred embodiment, the working and reference electrodes are both protected by locating them within one or more reservoirs. This may be a preferred configuration for an implantable sensor device. The reference electrode may be in close proximity to the working electrode and may be protected from environmental degradation by the reservoir cap.

The working electrode in the reservoir includes, e.g., is covered completely or at least partially by, an appropriate analyte sensor chemistry. The reference electrode may or may not be covered by the sensor chemistry. In one embodiment, it may be preferable or simpler to deposit the chemistry over both electrodes, and in this way the reference electrode may be considered to be measuring the environment seen by the working electrode. However this may not be desirable for certain embodiments where the composition of the reference electrode is such that it reacts or interferes with sensor chemistry. For example, silver ions from a silver/silver chloride reference electrode may inhibit glucose oxidase activity. In such embodiments, the sensor chemistry preferably is applied to cover only the working electrode. It can facilitate depositing a sensor chemistry over an electrode to first surround the electrode with a barrier as conventionally known, for example, as shown in U.S. Pat. No. 5,376,255 to Gumbrecht, et al.

Figure 4:
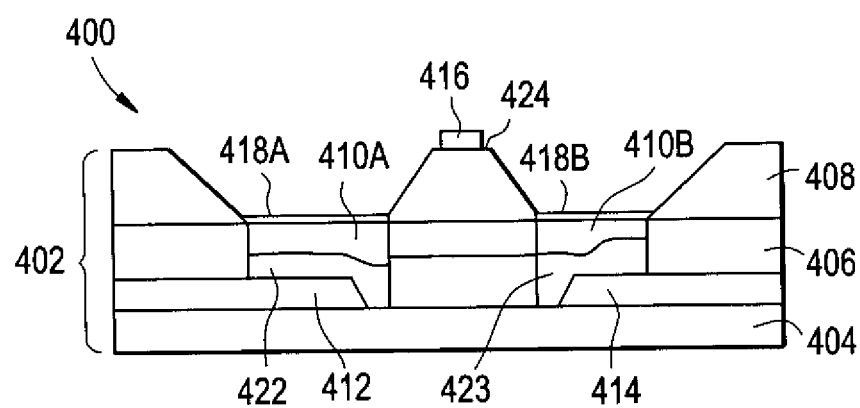
FIG. 4 is a side cross-sectional view of an embodiment of an amperometric sensor device.

The nature and placement of the auxiliary electrode outside of the reservoir may be varied. For example, it may be located on a lower substrate portion, coplanar with the working and reference electrodes, or it could be on a surface of an upper substrate portion. (The term "upper substrate portion" as used herein may be referred to in the art as a "microchip" or "microchip portion," as this substrate may include electronic circuitry for operation/actuation of reservoir cap disintegration.) In one embodiment, the portions of the reservoir caps remaining after activation, e.g., following electrothermal ablation, and the electrical traces connecting to the reservoir caps may be utilized as the auxiliary electrode. In another embodiment, as shown in FIG. 4, the auxiliary electrode is located on a surface of the upper substrate portion of the reservoir device, but is electrically isolated from the reservoir caps or traces connected to the reservoir caps. In yet another embodiment, an auxiliary electrode "external" to the sensor and reservoir substrates, such as a wire lead or the electronics case may be used. It may be advantageous to locate the auxiliary electrode outside of the reservoir, to minimize the interaction between redox reactions occurring at the auxiliary electrode and reactions taking place at the working electrode. A reason to separate the electrodes is that oxygen may be consumed at the auxiliary electrode which may otherwise limit the amount of oxygen available in the enzyme layer at the working electrode for glucose oxidation.

In another embodiment, the reference electrode and the working electrode are provided in separate reservoirs. This may be less desirable from the standpoint of having the reference electrode close to the working electrode, but may be desirable where the lifetime of the reference electrode is considerably greater than the working electrode, such that a single reference electrode could be used with a succession of working electrodes. In one embodiment, a single reference electrode (and a single auxiliary electrode) may be used with a two working electrodes operating simultaneously, in a configuration under control of a bipotentiostat. In another embodiment, a single reference electrode (and a single auxiliary electrode) may be used with more than two working electrodes operating simultaneously. Similarly, one auxiliary electrode may be used with more than one working electrode.

Examples of various embodiments of the amperometric sensor devices are illustrated in FIGS. 1-11. These are not drawn to scale. The shapes and dimensions of the electrodes, the reservoirs, the reservoir openings, the sensor chemistries, the substrates, and the bonding layers, if any, may be varied as needed to accommodate device specifications and manufacturing design constraints. It is to be understood from the figures that show only a single reservoir, that, in certain embodiments, a sensor device would include a structural body comprising an array of multiple such representative reservoirs/sensors.

FIG. 1 shows one embodiment of an amperometric sensor device 100. The device 100 generally includes a structural body or substrate 102. In the illustrated embodiment, the structural body 102 includes a lower substrate portion or base layer 104, an intermediate substrate portion or bonding layer 106, and an upper substrate portion 108. A reservoir 110 is formed in the substrate 102. Although only one reservoir 110 is shown, an array of reservoirs 110 may be provided. These reservoirs 110 may be, for example, identical and discrete, although other configurations are possible.

The amperometric sensor device 100 also includes a working electrode 112, a reference electrode 114, and an auxiliary electrode 116. As shown, the working electrode 112 and the reference electrode 114 are disposed within the reservoir 110, and the auxiliary electrode 116 is provided outside of the reservoir 110. A reservoir cap 118 covers an opening in the reservoir 110. The reservoir cap 118 may be electrically conductive, and traces or leads 120 may be provided for directing electric current through the reservoir cap 118. In the illustrated embodiment, the traces or leads 120 may serve as the auxiliary electrode 116 to conserve space. Such a configuration may require the ability to switch the connection of the reservoir cap 118 and traces or leads 120 from the reservoir cap activation electronics to the sensor electronics, but other configurations are possible.

The device 100 further includes sensor chemistry 122 located in the reservoir 110. The sensor chemistry 122 may include, for example, an enzyme and one or more polymer layers, such as those useful as semi-permeable membranes to permit passage of an analyte of interest therethrough while excluding certain other molecules. As shown, the sensor chemistry 122 may be deposited on both the working electrode 112 and the reference electrode 114, so that the reference electrode 114 is exposed to (i.e. "sees") the same environment as the working electrode 112, although in other embodiments the sensor chemistry 122 may not be deposited on the reference electrode 114.

The amperometric sensor device 100 also includes power and control systems (not shown) that power and control disintegration of the reservoir cap 118 and operatively couple to the electrodes. The power and control systems may be provided in a hardwired or wireless manner, for example, as described in U.S. Pat. No. 7,226,442 and U.S. Patent Application Publication No. 2005/0096587.

The illustrated embodiment of the device 100 includes a single set of electrodes 112, 114, 116 associated with a single reservoir 102, forming a sensor. In other embodiments, the device 100 may include an array of reservoirs 110. For example, the device 100 may include a number of identical, discrete reservoirs 110 that may be opened sequentially, such as one at a time, as a preceding exposed sensor becomes fouled and a fresh sensor is needed.

Figure 2:
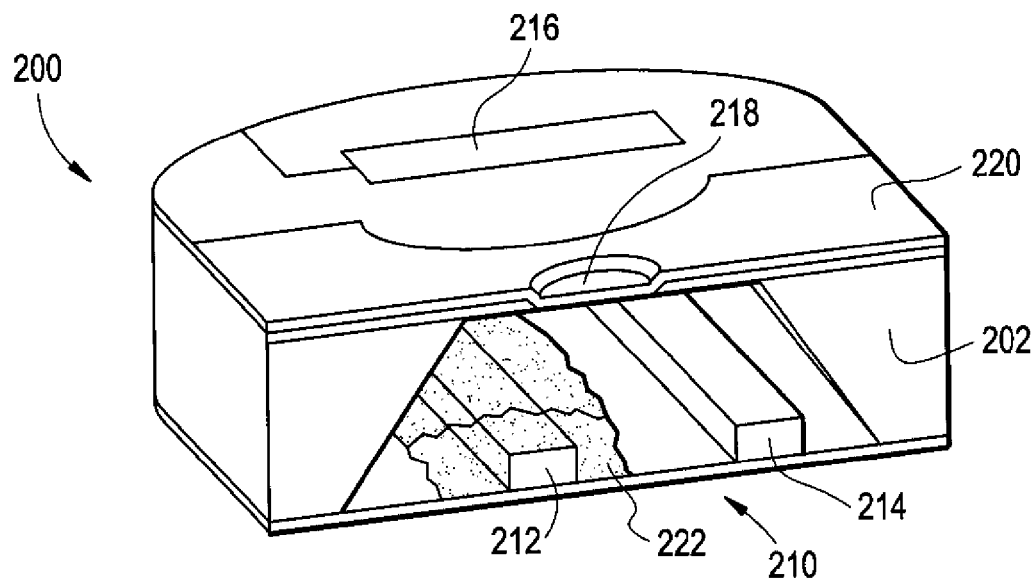
FIG. 2 is a partial cut-away, perspective view of an embodiment of an amperometric sensor device.

FIG. 2 shows an alternative embodiment of an amperometric sensor device 200, in which the working electrode 212 and the reference electrode 214 are located in a single reservoir 210, but the auxiliary electrode 216, which is outside of the reservoir 210, is a separate structural component from the reservoir cap 218 and its traces or leads 220. In certain cases, this may be a preferred embodiment, for example, in order to protect both the working electrode 212 and the reference electrode 214 inside the reservoir 210, or to position the reference electrode 214 and the working electrode 212 in close proximity to one another for operational purposes (e.g., so that they experience the same local microenvironment following reservoir opening) or to achieve both of these objectives. Note that in FIG. 2, the sensor chemistry 222 is not deposited on the reference electrode 214, although other configurations are possible. In this embodiment, the sidewalls of the reservoir taper toward the reservoir opening/reservoir cap. The material used for the upper substrate portion and the preferred means of creating the reservoir within that material may influence the slope of the sidewalls. For example, deep reactive ion etching (DRIE) of silicon produces vertical reservoir sidewalls.

Figure 3:
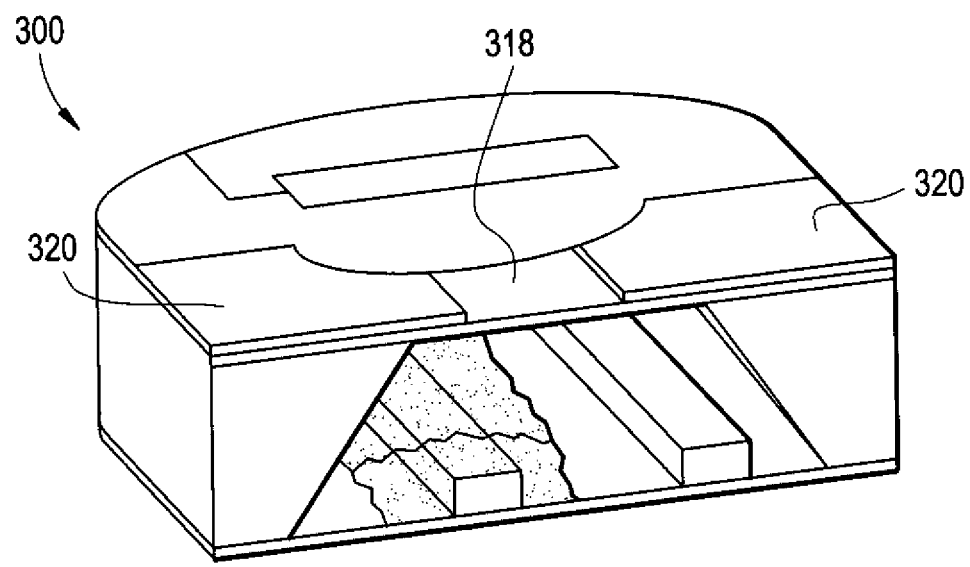
FIG. 3 is a partial cut-away, perspective view of an embodiment of an amperometric sensor device.

FIG. 3 shows an embodiment of an amperometric sensor device 300, which is a particular variation of the device 200 shown in FIG. 2. As shown, the reservoir cap 318 may have a different composition than the traces or leads 320 connected to the reservoir cap 318.

FIG. 4 shows another embodiment of the amperometric sensor device 400. The structural body or substrate 402 includes the portions 404, 406, 408 described above, but two reservoirs 410 are formed in the structural body 402 adjacent to each other. Specifically, a working electrode reservoir 410A is provided for the working electrode 412, while a reference electrode reservoir 410B is provided for the reference electrode 414. In this embodiment, the sensor chemistry 422 is deposited on the working electrode 412 in the working electrode reservoir 410A, and one or more polymer layers 423 are deposited on the reference electrode 414 in the reference electrode reservoir 410B. The polymer layers 423 may or may not be formed from similar components as the sensor chemistry 422, so that the reference electrode 414 in the reference electrode reservoir 410B is exposed to a similar environment as the working electrode 412 in the working electrode reservoir 410A.

The auxiliary electrode 416 is positioned outside of the reservoirs 410. For example, the auxiliary electrode 416 may be located on an outer surface 424 of the upper substrate portion 408, between the working electrode reservoir 410A and the reference electrode reservoir 410B, so that the auxiliary electrode 416 is in operable proximity to the working electrode 412 and/or reference electrode 414. The working, reference, and auxiliary electrodes in use are in intimate contact with the body fluid such that there is a path of relatively low electrical resistance between them. Traces or leads may be connected to the reservoir cap 418 in some embodiments, although the traces or leads are not shown in FIG. 4.

Figure 5:
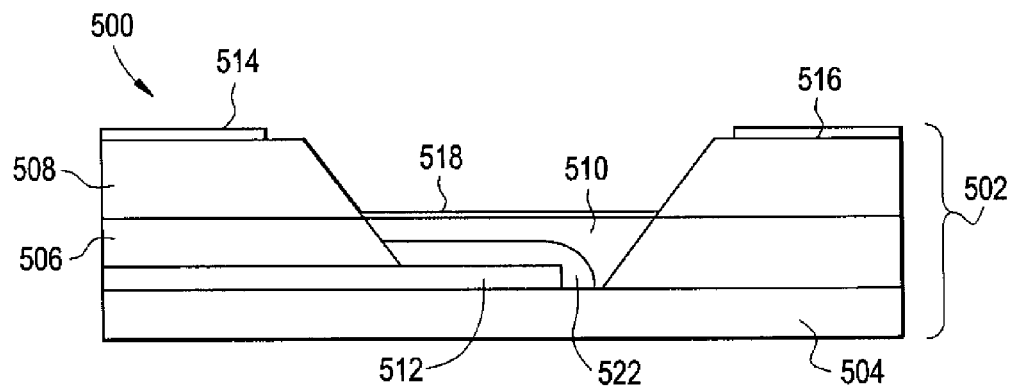
FIG. 5 is a side cross-sectional view of another embodiment of an amperometric sensor device.

FIG. 5 illustrates yet another embodiment of the amperometric sensor device 500. As shown, the structural body or substrate 502 includes the portions 504, 506, 508 described above, and one reservoir 510 is formed in the structural body 502. The working electrode 512 and the sensor chemistry 522 are located in the reservoir 510, while the reference electrode 514 and the auxiliary electrode 516 are located outside of the reservoir 510 on the same side of the structural body 502 as the reservoir cap 518.

Figure 6:
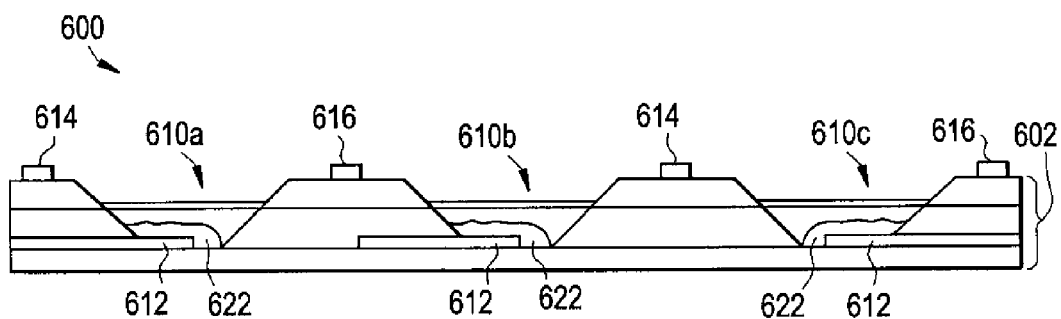
FIG. 6 is a side cross-sectional view of another embodiment of an amperometric sensor device.

FIG. 6 illustrates another embodiment of an amperometric sensor device 600. A number of reservoirs 610, such as three reservoirs 610A, 610B, and 610C, are formed in the structural body 602. A working electrode 612 and sensor chemistry 622 are located in each reservoir 610, while reference electrodes 614 and auxiliary electrodes 616 are located outside of the reservoirs 610. As shown, there does not need to be a one-to-one correspondence between the number of auxiliary electrodes 616 or reference electrodes 614 and the number of reservoirs 610. That is, two or more reservoirs 610 could share an auxiliary electrode 616, a reference electrode 614 or both.

Figure 7:
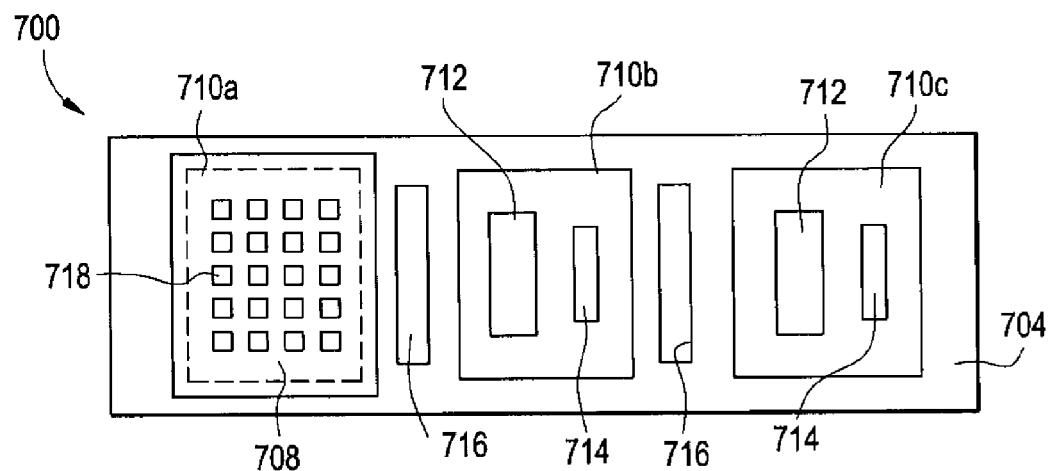
FIG. 7 is a top plan view of an embodiment of an amperometric sensor device.

FIG. 7 shows an embodiment of an amperometric sensor device 700 having an array of reservoirs, such as three reservoirs 710A, 710B, and 710C. Each reservoirs 710 contains a working electrode 712, a reference electrode 714, and sensor chemistry. Auxiliary electrodes 716 are provided outside of the reservoirs 710, such as between adjacent reservoirs 710. For example, one auxiliary electrode 716 is provided between reservoir 710A and reservoir 710B, and another auxiliary electrode 716 is provided between reservoir 710B and reservoir 710C. The auxiliary electrodes are positioned on the lower substrate portion or base layer 704. An upper substrate portion 708 is positioned above each reservoir 710. Note that for illustrative purposes the upper substrate portion 708 is shown over reservoir 710A, concealing the reservoir contents, while the upper substrate portion 708 is not shown over the remaining reservoirs 710B, 710C so that the reservoir contents can be seen (although the sensor chemistry is omitted for clarity).

The upper substrate portion 708 includes an array of apertures that serve as reservoir openings. A series of discrete reservoir caps 718 close the reservoir openings to seal in the working electrode 712, the reference electrode 714, and the sensor chemistry. For the purpose of example, a 4×5 array of apertures and twenty corresponding discrete reservoir caps are shown here. The seal formed by the reservoir caps 718 may be hermetic.

An example of the upper substrate portion 708 and reservoir cap 718 structure is described in U.S. Patent Application Publication No. 2006/0057737, which is incorporated herein by reference. In this way, an individual reservoir may have at least two reservoir openings with a support structure therebetween and closed by two or more reservoir caps covering the openings to control exposure of the electrode(s) within that reservoir. In one embodiment, the substrate comprises at least one reservoir cap support extending over the reservoir contents, wherein the two or more reservoir caps are in part supported by the at least one reservoir cap support. In one embodiment, a sensor device may comprise an array of two or more of such reservoirs, each having multiple reservoir openings. The reservoir cap supports can comprise substrate material, structural material, or coating material, or combinations thereof. The reservoir cap support(s) may be integral with upper substrate portion. Alternatively, the reservoir cap support may be made from a coating or deposited material distinct from the substrate portion. Reservoir cap supports comprising substrate material may be formed in the same step as the reservoirs. MEMS methods, microfabrication, micromolding, and micromachining techniques described herein or known in the art may be used to fabricate the substrate/reservoirs, as well as reservoir cap supports, from a variety of substrate materials.

Figure 8:
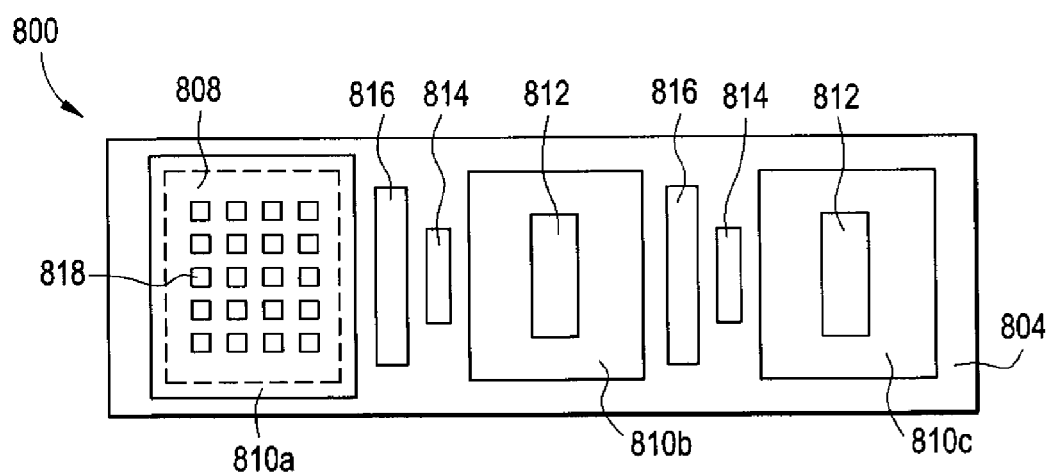
FIG. 8 is a top plan view of an embodiment of an amperometric sensor device.

FIG. 8 shows an embodiment of an amperometric sensor device 800 having an array of reservoirs 810, such as three reservoirs 810A, 810B, and 810C. Each reservoirs 810 contains a working electrode 812 and sensor chemistry (not shown). At least one reference electrode 814 and at least one auxiliary electrode 816 are provided outside of the reservoirs 810, such as between adjacent reservoirs 810. These may be shared. For example, one reference electrode 814 and one auxiliary electrode 816 are provided between reservoir 810A and reservoir 810B, which may shared by the working electrodes in these reservoirs 810A, 810B.

Figure 9:
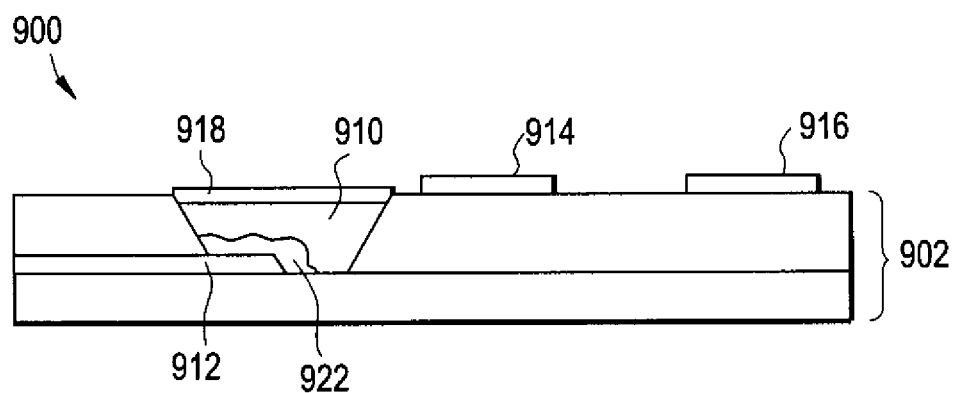
FIG. 9 is a side cross-sectional view of another embodiment of an amperometric sensor device.
Figure 10:
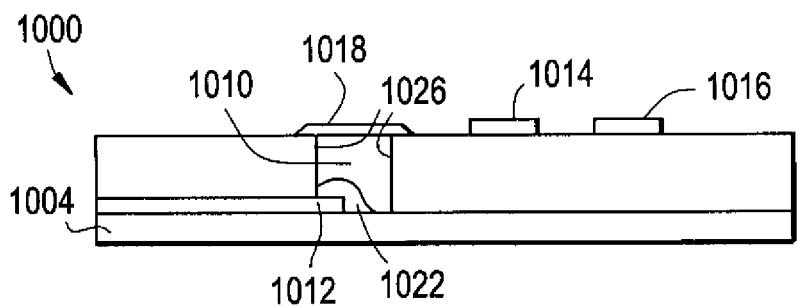
FIG. 10 is a side cross-sectional view of an embodiment of an amperometric sensor device.

FIG. 9 shows an embodiment of an amperometric sensor device 900 having the working electrode 912 and the sensor chemistry 922 located in the reservoir 910, and the reference electrode 914 and the auxiliary electrode 916 located outside of the reservoir 910. For example, the reference electrode 914 and the auxiliary electrode 916 may be located on the same side of the device 900 as the reservoir cap 918. Because resistive potential drops can be reduced by placing the working electrode 912 in close proximity to the reference electrode 914, the electrodes may be positioned so that the working electrode 912 is relatively closer to the reference electrode 914 than the auxiliary electrode 916. FIG. 10 shows an amperometric sensor device 1000 that is a variation of the device 900 shown in FIG. 9. Like the device 900, the working electrode 1012 and the sensor chemistry 1022 are located in the reservoir 1010, and the reference electrode 1014 and the auxiliary electrode 1016 are located outside of the reservoir 1010. The reservoir 1010 has sidewalls 1026 that are substantially perpendicular to the plane of the lower substrate portion or base layer 1004. Such reservoirs 1010 may be made using techniques described for example in U.S. Patent Application Publication No. 2006/0105275 to Maloney et al. An intermediate substrate portion or bonding layer is not shown in FIG. 10, although it is contemplated that such a layer could be included in this embodiment.

Figure 11:
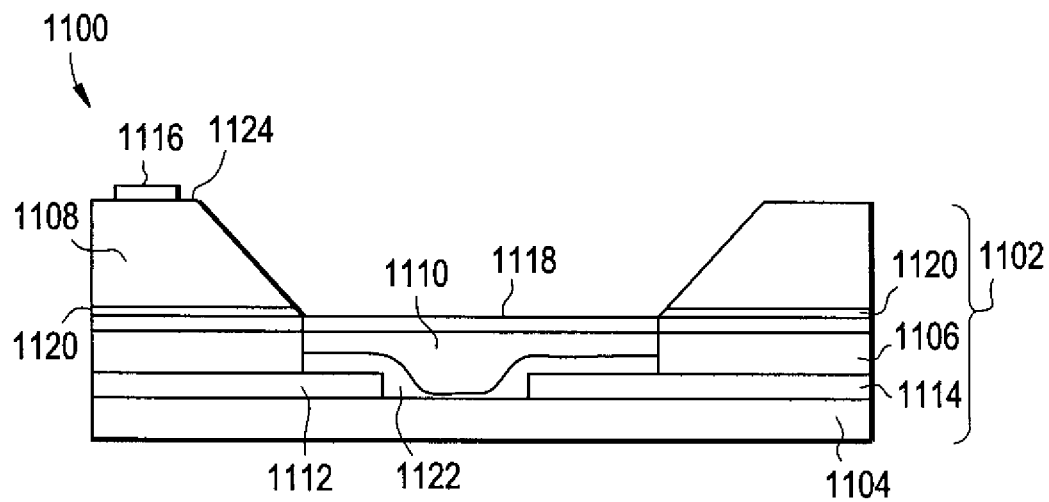
FIG. 11 is a side cross-sectional view of an embodiment of an amperometric sensor device.

FIG. 11 shows another embodiment of an amperometric sensor device 1100. The structural body or substrate 1102 includes the portions 1104, 1106, 1108 described above, and a reservoir 1110 is formed in the structural body 1102. The working electrode 1112, the reference electrode 1114, and the sensor chemistry 1122 are located in the reservoir 1110, and the auxiliary electrode 1116 is provided outside of the reservoir 1110. In this embodiment, which may be referred to as a "flip chip" design, the leads 1120 and other circuitry for the reservoir cap 1118 are located between the intermediate substrate portion 1106 and the upper substrate portion 1108, such that they are protected. The auxiliary electrode 1116 may be provided on the outer surface 1124 of the upper substrate portion 1108, distal to the reservoir cap 1118 and the associated leads 1120.

Although a single reservoir is shown in several of the embodiments described above and illustrated in the appended drawings, it is understood that the sensor device may include an array of multiple reservoirs, such as, two, four, ten, twenty, or one hundred reservoirs, each reservoir being associated with a discrete or shared combination of electrodes to form a sensor. Likewise, other combinations of substrate structures, reservoir shapes/sidewall angles, reservoir cap disintegration means, and the like, besides the particular combinations illustrated and described herein, are contemplated.

Potentiometric Sensor Device

In another aspect, the sensor device includes a potentiometric biosensor. A potentiometric biosensor measures the electric potential developed between an indicator electrode and a reference electrode. A common type of potentiometric biosensor includes an ion-selective electrode, for example, those responding to potassium, sodium, calcium, and hydrogen ions (effectively the pH of the solution). The electric potential typically exhibits a direct logarithmic relationship with the ion concentration in the analyte of interest, and in a particular embodiment, typically has a 60 millivolt per decade slope like that characteristic of the Nernst equation.

Some potentiometric sensors are constructed to include ion-selective electrodes (ISEs). The indicator electrode of ISEs, and in particular microfabricated ISEs, incorporates an ionophore into a polymer membrane. Sensor performance can degrade with time if the ionophore diffuses out of the membrane into the environment. Reference electrodes are also subject to degradation upon exposure to the in vivo environment. These issues may be addressed as described in U.S. Pat. No. 7,373,195 to Ye et al., in which a potassium indicator electrode is referenced against a sodium reference electrode. For example, enzyme layers may be coupled to ion-selective electrodes to create sensors for analytes such as urea, where the enzyme urease is immobilized on an ammonium ion-selective electrode. A Severinghaus electrode for measuring carbon dioxide is another type of potentiometric sensor that could be configured with the present devices.

A long-term implantable monitor based on microchip reservoir technology may include an array of complete sensors (i.e., fixed indicator/reference pairs), or separate arrays of indicator and reference electrodes. In the first case, where a complete sensor is contained within a single reservoir, the lifetime of the sensor will be determined by the shorter of the indicator and reference electrode lifetimes. With separate arrays, the indicator or reference electrode could be replaced as needed while the other remains in use.

Figure 12:
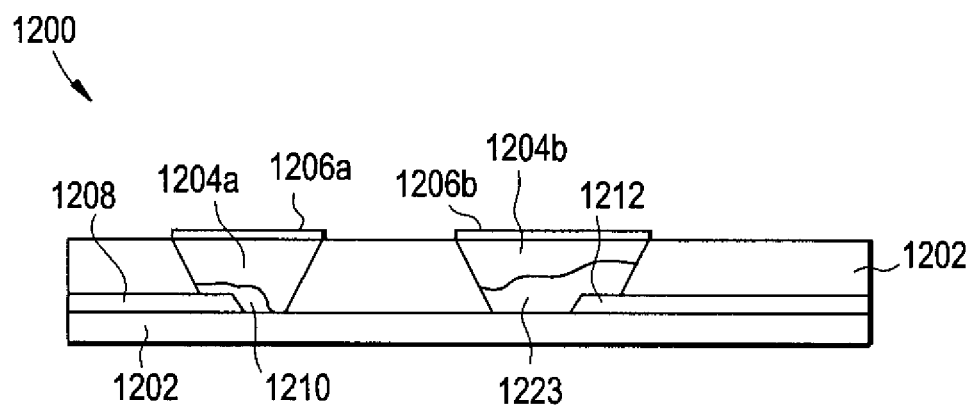
FIG. 12 is a side cross-sectional view of an embodiment of a potentiometric sensor device.

FIG. 12 illustrates a cross-sectional view of one embodiment of a potentiometric sensor device 1200. The potentiometric sensor device 1200 includes a substrate 1202 and one or more reservoirs 1204 formed in the substrate 1202. Each of the reservoirs 1204 is enclosed by a reservoir cap 1206. In the illustrated embodiment, two reservoirs 1204A and 1204B are enclosed by two separate reservoir caps 1206A and 1206B. An indicator electrode 1208 and sensor chemistry 1210 are located in one of the reservoirs 1204A, and a reference electrode 1212 and one or more polymer layers 1223 are located in the other reservoir 1204B. An intermediate substrate portion or bonding layer is not shown in FIG. 12, although it is contemplated that such a layer could be included in this embodiment. Alternatively, the indicator electrode 1208 and the reference electrode 1212 could be located in the same reservoir 1204. In one embodiment, the device may include first and second indicator electrodes, which could be configured to measure the same or different ionic species, e.g., potassium ions or sodium ions. The first and second indicator electrodes could be in the same reservoir or separate reservoirs.

Figure 13:
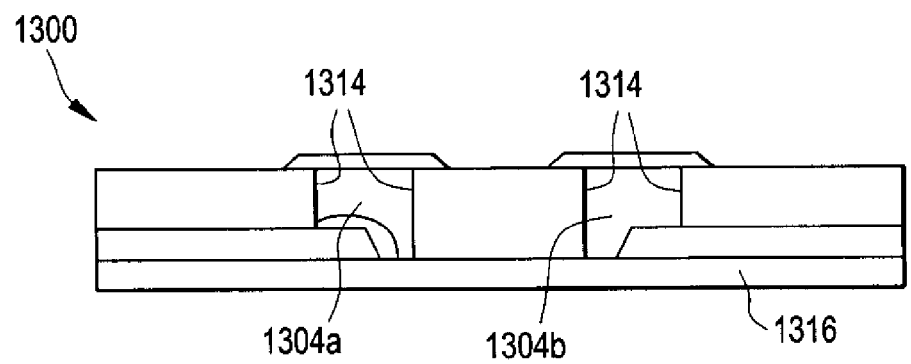
FIG. 13 is a side cross-sectional view of another embodiment of a potentiometric sensor device.

FIG. 13 illustrates an embodiment of a potentiometric sensor device 1300 that is similar the embodiment of the device 1200 shown in FIG. 12, except that the reservoirs 1304A and 1304B have sidewalls 1314 that are substantially perpendicular to the plane of a base substrate portion 1316. Such reservoirs 1304A and 1304B may be made using techniques described for example in U.S. Patent Application Publication No. 2006/0105275 to Maloney et al., which is incorporated herein by reference. An intermediate substrate portion or bonding layer is not shown in FIG. 13, although it is contemplated that such a layer could be included in this embodiment.

Field-Effect Transistor Sensor Device

A variation on the potentiometric sensor device is a device commonly known as an ion-sensitive field-effect transistor (ISFET) in which an ion-selective membrane of the type commonly used in the construction of indicator electrodes is used in place of the gate of a field-effect transistor. These devices also require a reference electrode. The ISFET and reference electrodes can be protected from the environment, such as the in vivo environment, by placing them in reservoirs, similar to the electrodes of the other types of chemical sensor devices described herein.

Conductometric Sensor Device

A conductometric biosensor, also known as an impedance biosensor, measures the electrical impedance or resistance between of a pair of electrodes each of which is coated with a biological recognition element such as an enzyme, antibody, biological receptor, or nucleic acid. Different from amperometric and potentiometric electrode configurations, the electrodes of a conductometric sensor typically consist of coplanar rectangular interdigitated or sepentine electrode pairs closely spaced as is known in the art. The pair of electrodes are coated with a biological recognition element such as an enzyme, antibody, biological receptor or nucleic acid. The pair of electrodes may also be coated with a selectively sensitive material, such as a polyimide for moisture sensing or a polymeric coating material for organic vapor sensing, as these are known in the art.

An identical set of electrodes, not coated with the reacting component, may be provided to increase the accuracy of the measurement by further sensing the electrical properties of the environment or sample of interest. These electrodes may be referred to herein as a control electrode pair, and may help to correct for nonspecific changes in impedance resulting from changes in factors such as temperature or analyte fluid conductivity. The control electrode pair optionally may be coated with a selectively permeable polymer material (without the biological recognition element).

The recognition-element coated interdigitated or serpentine pair of electrodes preferably are located inside the reservoirs. If using a control interdigitated electrode pair, it preferably is located within the same reservoir so as to ensure the matching of the active and control sensors. In one embodiment, the device includes an array of two or more discrete reservoirs that can be independently actively opened, wherein each reservoir contains one active and one control sensor.

Figure 14:
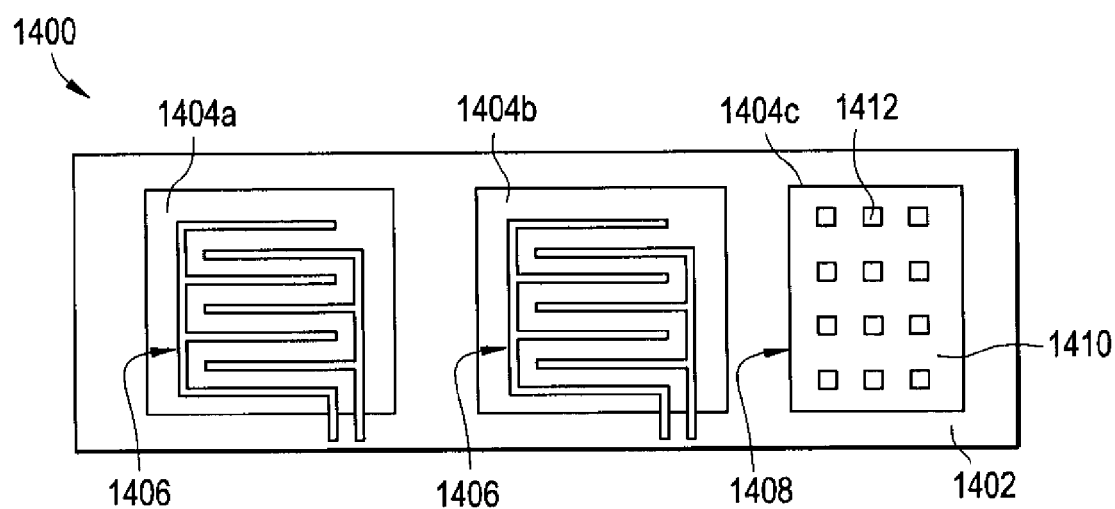
FIG. 14 is a top plan view of an embodiment of a conductometric sensor device.

FIG. 14 shows, in a plan view, one embodiment of a conductometric sensor device 1400 having a base substrate 1402 with an array of three reservoirs 1404A, 1404B, 1404C. Each reservoir 1404 contains an interdigitated pair of electrodes 1406, although the electrodes of the pair 1406 could have other shapes. An upper substrate/reservoir cap portion 1408 closes each reservoir 1404. Reservoirs 1404A, 1404B are shown without the corresponding upper substrate/reservoir cap portions 1408 so that the corresponding interdigitated pairs of electrodes 1406 can be seen. The upper substrate/reservoir cap portion 1408 of the reservoir 1404C includes an upper substrate 1410 having an array of apertures, which serve as reservoir openings. Corresponding discrete reservoir caps 1412 close off the reservoir openings, forming a seal over the electrodes 1406, which may be hermetic. As shown, the upper substrate 1410 includes a 3×4 array of apertures, and twelve corresponding reservoir caps 1412, although other arrangements are possible. An example of the upper substrate/reservoir cap portion 1408 is described in U.S. Patent Application Publication No. 2006/0057737. It is contemplated that the pair of electrodes 1406 is coated with at least the biological recognition element, and may be coated with other selectively sensitive material.

Figure 15:
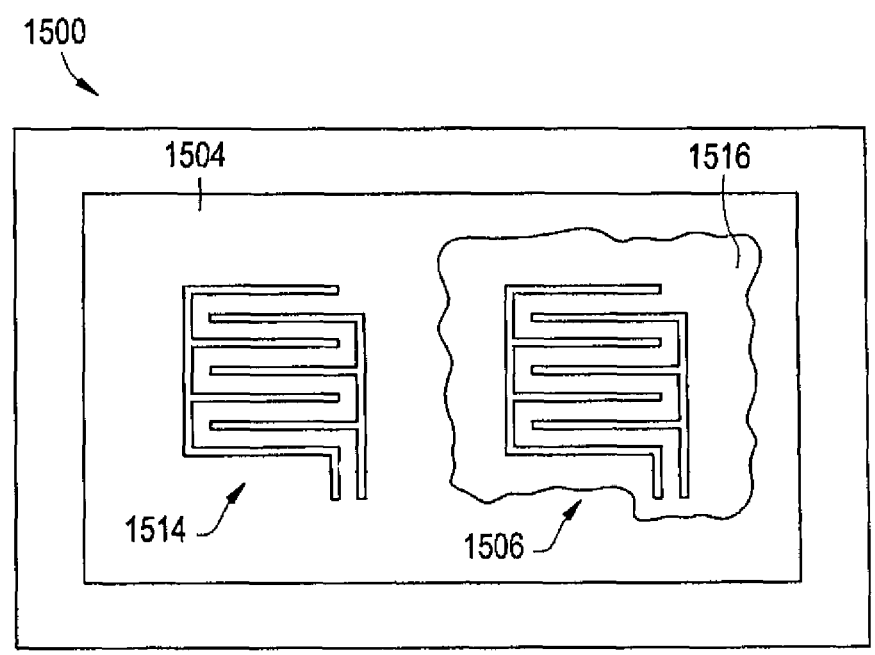
FIG. 15 is a top plan view of an embodiment of a conductometric sensor device.

FIG. 15 shows, in plan view, another embodiment of a conductometric sensor device 1500, illustrating an active pair of electrodes 1506 and a control pair of electrodes 1514 in a single reservoir 1504. The biological recognition element 1516 covers the active pair of electrodes 1506 but not the control pair of electrodes 1514. It is understood that the sensor devices described herein may be used as or adapted for inclusion in (e.g., included as part of) a medical device, such as an implantable medical device. In a non-limiting example, the implantable medical device may include an array of several sensors for long term sensing applications, such as glucose sensing, which would be useful for example in the management of a patient's diabetes. In another embodiment, the sensor device may be integrated into the end portion of a medical catheter intended for insert to the body of a patient for therapeutic or diagnostic purposes. It is contemplated that a sensor device, such as an implantable medical device or other medical device, may include various combinations of the sensor types and configurations described herein. For example, a single device, such as an implantable device, may include multiple different sensors. In one particular example, such a device may include an amperometric sensor (e.g., configured as a glucose sensor), a potentiometric sensor (e.g., configured as a potassium sensor), and a conductometric sensor (e.g., configured as an immunosensor for a cardiac biomarker).

It is also understood that the sensor devices described herein may be used as or adapted for inclusion in non-medical devices and systems. For example, the sensors may be used as environmental sensors, which may have a number of particular applications. In one case, the devices may be used to sense heavy metals or other pollutants in bodies of water, such as lakes and streams. In another case, the devices may be used to detect biological weapon agents. Such devices could be adapted to be fixed or mobile, for use in public venues, as a wearable device on first responders, in public transit systems, airports, on military vehicles, etc.

All documents cited in the Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Modifications and variations of the methods and devices described herein will be obvious to those skilled in the art from the foregoing detailed description. Such modifications and variations are intended to come within the scope of the appended claims.

What is claimed is:

1. An amperometric sensor device comprising:
  a structural body which comprises a first plurality of reservoirs, each of the first plurality of reservoirs having at least one opening in the structural body and a working electrode located in said reservoir;
  analyte sensor chemistry located within each of the first plurality of reservoirs and deposited on at least the working electrode;
  one or more auxiliary electrodes located on the structural body outside of the first plurality of reservoirs and a reference electrode located inside each reservoir, or one or more auxiliary electrodes located on the structural body outside of the first plurality of reservoirs and one or more reference electrodes located outside of the first plurality of reservoirs;
  at least one reservoir cap closing the at least one opening of each of the first plurality of reservoirs to isolate the working electrode and analyte sensor chemistry within the reservoir from an analyte outside of the reservoir to prevent contact with the analyte sensor chemistry; and
  means for rupturing or displacing each reservoir cap independently to permit the analyte from outside of the reservoir to contact the analyte sensor chemistry,
  wherein the one or more reference electrodes, the one or more auxiliary electrodes, or both, are adapted to be operatively coupled with two or more of the working electrodes.

2. The amperometric sensor device of claim 1, wherein the analyte sensor chemistry is further deposited on the reference electrode.

3. The amperometric sensor device of claim 1, wherein the one or more reference electrodes are located outside of the first plurality of reservoirs and in one or more of a second plurality of reservoirs separate from the first plurality of reservoirs containing the working electrodes.

4. The amperometric sensor device of claim 1, wherein the analyte sensor chemistry comprises an enzyme-containing layer and at least one polymer layer.

5. The amperometric sensor device of claim 4, wherein an enzyme of the enzyme-containing layer is selected from the group consisting of glucose oxidase, glucose dehydrogenase, NADH oxidase, uricase, urease, creatininase, sarcosine oxidase, creatinase, creatine kinase, creatine amidohydrolase, cholesterol esterase, cholesterol oxidase, glycerol kinase, hexokinase, glycerol-3-phosphate oxidase, lactate oxidase, lactate dehydrogenase, alkaline phosphatase, alanine transaminase, aspartate transaminase, amylase, lipase, esterase, gamma-glutamyl transpeptidase, L-glutamate oxidase, pyruvate oxidase, diaphorase, bilirubin oxidase, and mixtures thereof.

6. The amperometric sensor device of claim 1, wherein each of the first plurality of reservoirs has two or more openings and two or more discrete reservoir caps, each reservoir cap closing at least one of the reservoir openings, and wherein the structural body further comprises at least one reservoir cap support extending over each reservoir, wherein the two or more reservoir caps are in part supported by the at least one reservoir cap support.

7. The amperometric sensor device of claim 1, wherein the area of each auxiliary electrode is equal to or larger than the area of each working electrode.

8. The amperometric sensor device of claim 1, wherein each means for rupturing or displacing comprises:
a pair of conductive leads electrically connected to the reservoir cap, the reservoir cap comprising an electrically conductive material; and
a power source for applying an electrical current through the reservoir cap via the pair of conductive leads,
wherein the pair of conductive leads and power source are adapted to rupture the reservoir cap by electrothermal ablation.

9. The amperometric sensor device of claim 8, wherein the pair of conductive leads, the reservoir cap, or both, serve as the auxiliary electrode.

10. The amperometric sensor device of claim 1, wherein each means for rupturing or displacing comprises a cathode and a source of electrical power, the reservoir cap serves as an anode, and the reservoir cap disintegrates upon application of an electric potential between the anode and the cathode.

11. A catheter comprising the amperometric sensor device of claim 1.

12. An implantable medical device comprising the amperometric sensor device of claim 1.

13. A potentiometric sensor device comprising:
a structural body which comprises a plurality of reservoirs that each have at least one opening in the structural body;
at least one indicator electrode located within a first reservoir of the plurality of reservoirs;
at least one reference electrode located within a second reservoir of the plurality of reservoirs, wherein the first reservoir is different from the second reservoir and the at least one indicator electrode and the at least one reference electrode forms an operable pair of electrodes;
at least one reservoir cap closing the at least one opening of each of the plurality of reservoirs, to isolate the at least one indicator electrode and the at least one reference electrode within the first and second reservoirs and to prevent an analyte outside of the first and second reservoirs from contacting the at least one indicator electrode and the at least one reference electrode; and
means for rupturing or displacing the reservoir caps independently to permit the analyte from outside of the reservoir to contact the at least one indicator electrode and the at least one reference electrode,
wherein an electrical potential which can be developed between the at least one indicator electrode and the at least one reference electrode provides a sensor signal indicative of a concentration of the analyte.

14. The potentiometric sensor device of claim 13, which comprises a plurality of the indicator electrodes, each one being located in a separate reservoir.

15. An implantable medical device comprising the potentiometric sensor device of claim 13.

16. A potentiometric sensor device comprising:
a structural body which comprises a first plurality of reservoirs that each have at least one opening in the structural body;
at least one indicator electrode located within each of the first plurality of reservoirs;
at least one reference electrode located outside of the first plurality of reservoirs;
at least one reservoir cap corresponding to and closing each of the at least one opening of each of the first plurality of reservoirs, to isolate the at least one indicator electrode within each of the plurality of reservoirs from an analyte outside of the reservoir to prevent contacting the at least one indicator electrode; and
means for rupturing or displacing each of the at least one reservoir cap independently to permit the analyte from outside of the reservoir to contact the at least one indicator electrode,
wherein a potential which can be developed between the at least one indicator electrode and the at least one reference electrode provides a sensor signal indicative of a concentration of the analyte.

17. The potentiometric sensor device of claim 16, which comprises a plurality of the indicator electrodes, each one being located in a separate reservoir.

18. An implantable medical device comprising the potentiometric sensor device of claim 16.

19. A conductometric sensor device comprising:
a structural body which comprises a plurality of reservoirs that each have at least one opening in the structural body;
an electrode pair located within each reservoir, each electrode pair being co-planar and having an interdigitated or serpentine configuration and at least one reference electrode located outside of the plurality of reservoirs;
a biological recognition element or other selectively sensitive material located within each reservoir and deposited on the electrode pair;
at least one reservoir cap closing the at least one opening of each reservoir to isolate the electrode pair and the biological recognition element within the reservoir from an analyte outside of the reservoir and to prevent contacting the biological recognition element; and
means for rupturing or displacing each reservoir cap independently to permit the analyte from outside of the reservoir to contact the corresponding biological recognition element.

20. The conductometric sensor device of claim 19, wherein the biological recognition element comprises an enzyme, an antibody, a nucleic acid, a receptor protein, or a combination thereof.

21. The conductometric sensor device of claim 19, wherein the other selectively sensitive material comprises a polyimide for moisture sensing.

22. The conductometric sensor device of claim 19, wherein the other selectively sensitive material comprises a polymeric coating material for organic vapor sensing.

23. An implantable medical device comprising the conductometric sensor device of claim 19.

24. The conductometric sensor device of claim 19, further comprising a control electrode pair.

25. The potentiometric sensor device of claim 16, wherein:
   each of the at least one reference electrodes is located within a reservoir of a second plurality of reservoirs, each reservoir of the second plurality of reservoirs having at least one opening in the structural body and at least one reservoir cap closing the at least one opening, to isolate the at least one reference electrode within the reservoir it is located within and to prevent an analyte outside of the reservoir from contacting the at least one reference electrode, and
   the device further comprises means for rupturing or displacing the at least one reservoir cap of the second plurality of reservoirs independently to permit the analyte from outside of the reservoir to contact the at least one reference electrode.

* * * * *